US00PP19819P2

(12) United States Plant Patent
Klemm

(10) Patent No.: US PP19,819 P2
(45) Date of Patent: Mar. 10, 2009

(54) ***PELARGONIUM* PLANT NAMED 'KLEPP07195'**

(50) Latin Name: *Pelargonium peltatum*
Varietal Denomination: KLEPP07195

(75) Inventor: Nils Klemm, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/077,381

(22) Filed: Mar. 19, 2008

(51) Int. Cl.
*A01H 5/00* (2006.01)

(52) U.S. Cl. ..... Plt./332

(58) Field of Classification Search ..... Plt./332
See application file for complete search history.

*Primary Examiner*—Annette H Para
(74) *Attorney, Agent, or Firm*—Jondle & Associates, P.C.

(57) ABSTRACT

A new cultivar of *Pelargonium* particularly characterized by white flowers with purple eyes, an ivy trailing habit with medium vigor, good outdoor performance and tolerance to heat and rain, is disclosed.

1 Drawing Sheet

Genus and species: *Pelargonium peltatum.*
Variety denomination: 'KLEPP07195'.

BACKGROUND OF THE NEW PLANT

The present invention comprises a new and distinct cultivar of *Pelargonium*, botanically known as *Pelargonium peltatum,* and hereinafter referred to by the cultivar name 'KLEPP07195'. 'KLEPP07195' was discovered as a seedling resulting from a cross in July 2003 in Stuttgart, Germany between the female parent, the proprietary *Pelargonium* plant 'CC-W 04' (unpatented) and the male parent, the proprietary *Pelargonium* plant 'P 22 061' (unpatented). A single plant selection was subsequently chosen for further evaluation and for asexual propagation.

The new cultivar was created in 2003 in Stuttgart, Germany and has been asexually reproduced repeatedly by vegetative cuttings in Stuttgart, Germany over a 4 and one-half-year period. 'KLEPP07195' has been found to retain its distinctive characteristics through successive asexual propagations.

Plant Breeder's Rights for this cultivar were applied for in Switzerland on Jul. 6, 2007. 'KLEPP07195' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. White flowers with purple eyes;
2. An ivy trailing habit with medium vigor;
3. Good outdoor performance; and
4. Tolerance to heat and rain.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures. The photograph is of a plant about 3-months old and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPP007195'. The data which define these characteristics were collected from asexual reproductions carried out in Stuttgart, Germany. The plant history was taken on 3-month old, un-pinched plants in 12-cm pots in a greenhouse in January through April. The color readings were determined under natural light. Color references are to the R.H.S. Colour Chart of The Royal Horticultural Society of London (R.H.S.) 2001).

DETAILED BOTANICAL DESCRIPTION

Classification:
- *Family.*—Geraniacaea.
- *Species.—Pelargonium peltatum.*
- *Common name.—Pelargonium* (*Geranium*), Ivy *geranium.*
- *Denomination.*—'KLEPP07195'.

Parentage:
- *Female parent.*—The proprietary *Pelargonium* plant 'CC-W 04' (unpatented).
- *Male parent.*—The proprietary *Pelargonium* plant 'P 22 061' (unpatented).

Plant:
- *Habit.*—Trailing.
- *Height.*—26 cm to 32 cm.
- *Spread.*—25 cm to 29 cm.
- *Life cycle.*—Perennial, but usually treated as an annual.
- *Form.*—Rounded, bushy; for use in baskets.
- *Time to produce a rooted cutting.*—18 to 20 days.
- *Time to bloom from propagation.*—Approximately 82 days.

Stems:
- *Stem color.*—RHS 137B.
- *Pubescence.*—Present.

*Stem form.*—Round.
*Diameter.*—0.5 cm to 1.3 cm.
*Length.*—5.0 cm to 15.0 cm.
*Interode length.*—0.8 cm to 1.4 cm.

Leaves:
*Arrangement.*—Alternate.
*Shape.*—Typical of ivy *geraniums*, kidney-shaped.
*Apex.*—Rounded.
*Base.*—Closed.
*Margin.*—Entire.
*Surface texture.*—Upper surface: Glossy. Lower surface: Dull with very short pubescence.
*Length.*—4.0 cm to 5.0 cm.
*Width.*—6.0 cm to 7.0 cm.
*Color.*—Upper surface: RHS 137A. Lower surface: RHS 137D.
*Petiole.*—Length: 5.0 cm to 7.0 cm. Diameter: 0.15 cm to 0.2 cm. Color: RHS 137D. Texture: Rough, slightly pubescent.
*Venation pattern.*—Palmate.
*Venation color.*—RHS 137D.
*Zonation color.*—RHS 177A.
*Zonation diameter.*—About 1.5 cm.

Inflorescence:
*Flowering habit.*—Continuous.
*Lastingness of inflorescence on the plant.*—10 to 16 days.
*Umbels.*—Length: 10.0 cm. Diameter: 12.0 cm.
*Individual florets of the umbel.*—Depth: 1.5 cm. Diameter: 3.5 cm to 4.0 cm.
*Fragrance.*—Absent.

Flower buds:
*Cluster shape.*—Umbelliferous.
*Length.*—0.5 cm to 1.0 cm.
*Width.*—0.3 cm to 0.6 cm.
*Texture.*—Rough.
*Bud.*—Shape: Elliptical. Apex: Acute. Base: Obtuse. Margin: Entire, smooth. Color: RHS 137C.

Petals:
*Quantity per flower.*—5 to 7.
*Shape.*—Ovate.
*Apex.*—Rounded.
*Base.*—Attenuate.
*Margin.*—Entire.
*Length.*—2.0 cm.
*Width.*—1.5 cm.
*Color of lobes* (*both upper and lower lobes*).—RHS 155D.

Sepals:
*Number per flower.*—5.
*Shape.*—Elliptic.
*Apex.*—Acute.
*Base.*—Obtuse.
*Margin.*—Entire.
*Color* (*both surfaces*).—RHS 137D.
*Length.*—0.8 cm to 1.0 cm.
*Width.*—0.3 cm to 0.6 cm.

Pedicel:
*Length.*—2.5 cm to 3.0 cm.
*Diameter.*—0.15 cm.
*Color.*—RHS 137D.
*Texture.*—Rough.

Peduncle:
*Length.*—14.0 cm to 15.0 cm.
*Diameter.*—0.2 cm.
*Color.*—RHS 137C.
*Texture.*—Rough.

Reproductive Organs:
*Stamens.*—Anther length: 0.3 cm. Filament length: 0.6 cm. Filament color: RHS 155C. Pollen amount: Moderate. Pollen color: RHS 33A.
*Pistils.*—Number: 1. Stigma color: RHS 74D.
*Style length.*—0.4 cm.
*Style color.*—RHS 155C.
*Ovary arrangement.*—Club shaped.

Fruit/seed set: None observed.

Disease and Insect Resistance: No particular disease or insect resistance noted.

COMPARISON WITH PARENTAL AND COMMERCIAL CULTIVARS

'KLEPP07195' differs from the female parent, the proprietary *Pelargonium* plant 'CC-W 04' (unpatented) in that 'KLEPP07195' has double flowers, green leaves and a medium growth habit, while 'CC-W 04' has single flowers, light-green leaves and a strong growth habit. Additionally, 'KLEPP07195' has a better branching habit than 'CC-W 04'.

'KLEPP07195' differs from the male parent, the proprietary *Pelargonium* plant 'P 22 061' (unpatented) in that 'KLEPP07195' has a medium growth habit, while 'P 22 061' has a strong (more vigorous) growth habit.

'KLEPP07195' differs from the commercial comparison variety 'Klegatta' (unpatented; disclosed in U.S. application Ser. No. 09/250,016, now abandoned), in that 'KLEPP07195' has white flowers with purple eyes, while 'Klegatta' has white flowers with light-pink stripes. Additionally, 'Klegatta' has a more compact growth habit than 'KLEPP07195'.

I claim:

1. A new and distinct cultivar of *Pelargonium* plant as shown and described herein.

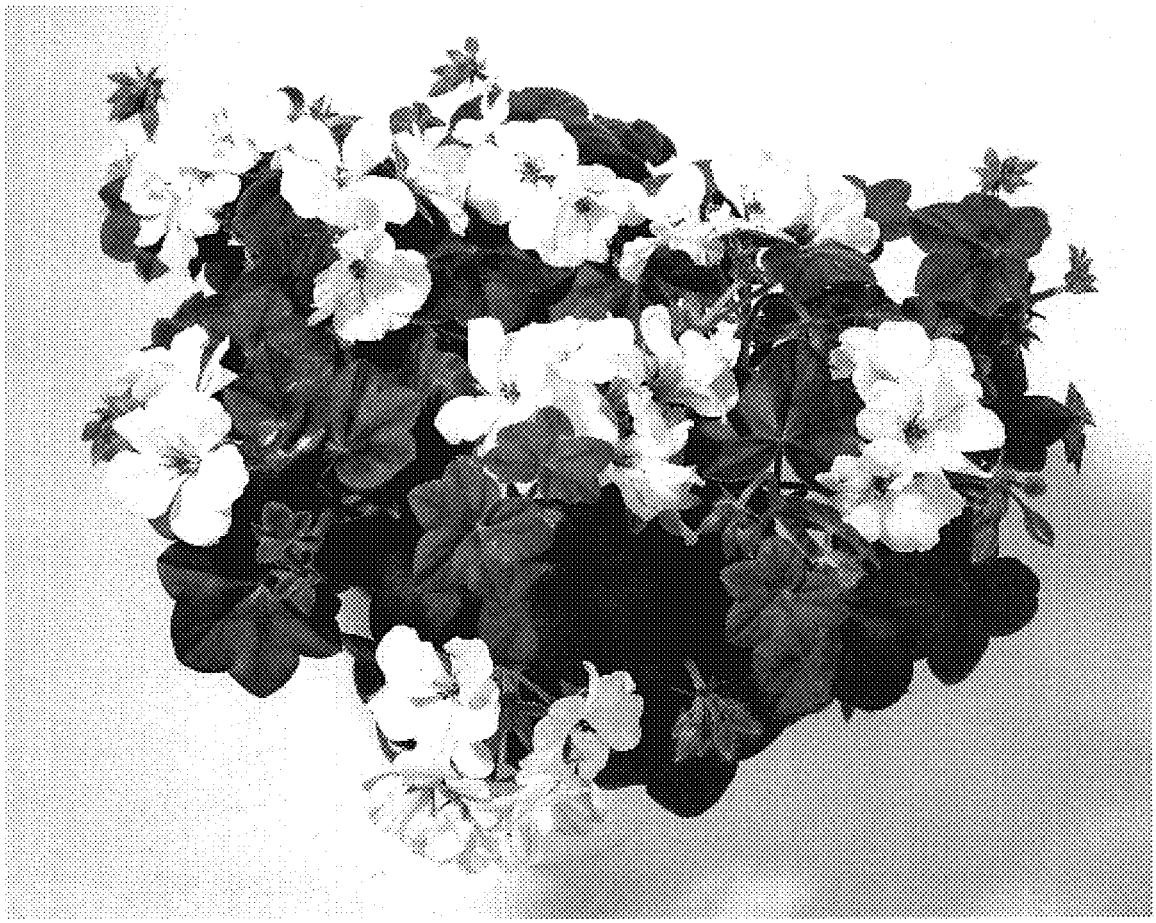

* * * * *